United States Patent [19]
Rogers et al.

[11] Patent Number: 5,578,190
[45] Date of Patent: Nov. 26, 1996

[54] PROCESS FOR THE PREPARATION OF GLYPHOSATE AND GLYPHOSATE DERIVATIVES

[75] Inventors: Thomas E. Rogers, Manchester; Lowell R. Smith, Kirkwood, both of Mo.

[73] Assignee: Monsanto Company, St. Louis, Mo.

[21] Appl. No.: 418,717

[22] Filed: Apr. 7, 1995

Related U.S. Application Data

[62] Division of Ser. No. 474,309, Feb. 5, 1990, which is a continuation of Ser. No. 158,816, Feb. 22, 1988, abandoned, which is a continuation-in-part of Ser. No. 687,305, Dec. 28, 1984, abandoned.

[51] Int. Cl.$^6$ ............................... C07F 9/38; C07F 9/40; C25B 3/00
[52] U.S. Cl. .............. 205/436; 558/145; 562/17
[58] Field of Search .......................... 558/145; 562/17; 204/74; 205/436

[56] References Cited

U.S. PATENT DOCUMENTS

| | | | |
|---|---|---|---|
| 3,103,473 | 9/1963 | Judo | 204/74 |
| 3,288,846 | 11/1966 | Irani et al. | 260/500 |
| 3,361,653 | 1/1968 | Miller | 204/74 |
| 3,799,758 | 3/1974 | Franz | 71/86 |
| 3,907,652 | 9/1975 | Wagenknecht et al. | 204/79 |
| 3,927,080 | 12/1975 | Gaertner | 260/502.5 |
| 3,969,398 | 7/1976 | Hershman | 260/502.5 |
| 4,062,669 | 12/1977 | Franz | 71/86 |
| 4,065,491 | 12/1977 | Pfliegel et al. | 260/502.5 |
| 4,094,928 | 6/1978 | Gaertner | 558/145 |
| 4,160,779 | 7/1979 | Maier | 260/502.5 |
| 4,237,065 | 12/1980 | Ehrat | 260/502.5 |
| 4,348,332 | 9/1982 | Oediger et al. | 260/502.4 R |
| 4,369,142 | 1/1983 | Moser | 260/502.5 F |
| 4,486,358 | 12/1984 | Moser | 260/502.5 F |
| 4,588,432 | 2/1986 | Rogers | 204/73 |

FOREIGN PATENT DOCUMENTS

| | | |
|---|---|---|
| 1039739 | 10/1978 | Canada . |
| 0079767 | 5/1983 | European Pat. Off. . |
| 0081459 | 6/1983 | European Pat. Off. . |
| 0186648 | 7/1986 | European Pat. Off. . |
| 0214578 | 3/1987 | European Pat. Off. . |
| 2294182 | 7/1976 | France . |

OTHER PUBLICATIONS

Wagner, Synthetic Org. Chemistry (1963), pp. 650–661.
Kihlberg et al., "Synthesis of Strombine. A New Method for Monocarboxymethylation of Primary Amines", *Acta. Chemica Scandinavica B* 37 (1983), pp. 911–916.
Kagaku Duijten (Encyclopedia Chemical), vol. 3 Kyoritau Schuppan (1960), pp. 86–87 with translation.
Saubastre, Proc. Amer. Electroplaster's Soc., vol. 42 (1959), pp. 264–276.
Gaylord, "Reduction with Complex Metal Hydrides" (1956), pp. 789, 790, and 806.
Ikutani, "Studies of the N–Oxides of N,N–Dialkylamino Acids II. The Synthesis of N,N–Dialkylglycine and Corresponding N–Oxides." The Synthesis Society of Japan, 42, pp. 2330–2332 (1969).
Bowman, "N–Substituted Amino–Acids. Part II, The Reduction of Alkylation of Amino–Acids", *Journal of The Chemical Society*, Part 2, pp. 1346–1349 (1950).
Wagenknecht, "An Electrochemical Method For The Preparation of Iminodimethylenediphosphonic Acid", *Syn. React. Inorg. Metal–Org. Chem.*, 4,(6), 567–572 (1974).
Yanagawa, "Novel Formation of α–Amino Acids and Their Derivatives From Oxo Acids and Ammonia in an Aqueous Medium", *J. Biochem.* 91 2087–2090 (1982).

*Primary Examiner*—Joseph E. Evans
*Attorney, Agent, or Firm*—Grace L. Bonner; Mark F. Wachter; Jon H. Beusen

[57] ABSTRACT

A process for preparing glyphosate and other secondary amines of related structure in which a precursor primary amine such as aminomethylphosphonic acid is condensed with glyoxylic acid, or a related aldehyde compound, and the condensation product reduced without isolation to produce the desired product.

13 Claims, 2 Drawing Sheets

PROCESS FOR THE PREPARATION OF GLYPHOSATE AND GLYPHOSATE DERIVATIVES

CROSS REFERENCES TO RELATED APPLICATIONS

The present application is a division of application Ser. No. 07/474,309 filed Feb. 5, 1990, which is a continuation of application Ser. No. 07/158,816 filed Feb. 22, 1988 (now abandoned), which in turn is a continuation-in-part of application Ser. No. 06/687,305 filed Dec. 28, 1984 (now abandoned).

BACKGROUND OF THE INVENTION

This invention relates to the synthesis of secondary amines containing phosphonyl and carbonyl groups and, more particularly, to an improved process for producing N-phosphonomethylglycine or derivatives thereof by reductive alkylation.

N-phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. Glyphosate and salts thereof are conveniently applied in an aqueous formulation as a post-emergent phytotoxicant or herbicide for the control of one or more monocotyledonous species and one or more dicotyledonous species. Moreover, such compounds are characterized by broad spectrum activity, i.e., they control the growth of a wide variety of plants, including but not limited to ferns, conifers, aquatic monocotyledons, and dicotyledons.

Hershman, U.S. Pat. No. 3,969,398, describes a process for preparing glyphosate in which iminodiacetic acid is reacted with formaldehyde and phosphorous acid to produce N-phosphonomethyliminodiacetic acid as an intermediate. This is then oxidized in the presence of a carbon catalyst to produce glyphosate.

Gaertner, Canadian Patent 1,039,739, describes a process for producing glyphosate by reacting aminomethylphosphonic acid and its esters with glyoxal or glyoxylic acid to form carbonylaldiminomethanephosphonates. Thereafter, the carbonylaldiminomethanephosphonates are subjected to catalytic hydrogenation to reduce the double bond and produce glyphosate acid or its esters. The ester groups are then hydrolyzed to produce N-phosphonomethylglycine. Both the condensation of aminomethylphosphonate with an aldehyde and catalytic hydrogenation of the resultant imine are carried out in organic solvents. For the condensation reaction the solvent is an aromatic hydrocarbon, such as benzene, toluene, or xylene, while catalytic hydrogenation is typically carried out in an alcohol.

Franz, U.S. Pat. No. 3,799,758, describes the preparation of glyphosate by reaction of ethyl glycinate, formaldehyde, and diethyl phosphite. Alternative processes described by Franz include phosphonomethylation of glycine with chloromethylphosphonic acid in the presence of sodium hydroxide and oxidation of N-phosphinomethylglycine with mercuric chloride.

Gaertner, U.S. Pat. No. 3,927,080, describes the production of glyphosate by acid hydrolysis and dealkylation of N-t-butyl-N-phosphonomethylglycine or its esters. Tertiary butyl amine is reacted with a bromoacetate ester to produce an ester of N-t-butyl-glycine, which is in turn reacted with formaldehyde and phosphorous acid to produce the N-t-butyl-N-phosphonomethylglycine precursor.

Ehrat, U.S. Pat. No. 4,237,065, describes a process in which N-phosphonomethylglycine is prepared starting from glycine, formaldehyde and a tertiary base in an alcoholic solution. After completion of the reaction, a dialkyl phosphite is added and the reaction product is hydrolyzed and then acidified to precipitate the product.

While Gaertner, as described in his aforesaid Canadian patent, achieved monoalkylation of aminomethylphosphonic acid by the sequential process of first condensing aminomethylphosphonic acid or its esters with glyoxylic acid and its esters to produce the aldimine and thereafter subjecting the aldimine to catalytic hydrogenation, there are other references which describe the in situ reduction of the condensation products of various amines and aldehydes. Such condensation and in situ reduction is generally referred to in the art as reductive alkylation. However, when the aldimino structure obtained by condensation of a primary amine with an aldehyde is reduced in situ, the resultant secondary amine can further react with the aldehyde to produce a hemiaminal or an aminal which is in turn reduced by hydrogenolysis, resulting in the formation of a tertiary amine. Thus, the result is typically substantial dialkylation rather than the substantially exclusive monoalkylation that is preferred in the preparation of an end product, such as glyphosate.

Ikutani, "Studies of the N-Oxides of N,N-Dialkyl Amino Acids. II. The Syntheses of N,N-Dialkylglycine and Corresponding N-Oxides", *Bulletin of the Chemical Society of Japan*, Volume 42, pp. 2330–2332, reports the reductive condensation of glycine with various aliphatic aldehydes. Only with relatively hindered aldehydes did Ikutani recover any monoalkylated product after reactions at 40° C. to 50° C. for periods of 3 to 9 hours. In the case of acetaldehyde, propionaldehyde, and N-butyraldehyde, at best a trace of monoalkyl product was recovered, while the dialkyl yields ranged from 41% to 83%.

Bowman, "N-Substituted Amino Acids. Part II. The Reductive Alkylation of Amino Acids", *Journal of the Chemical Society* (1950), p. 1346, reported that experiments on the alkylation of glycine by means of acetaldehyde, propionaldehyde, N-butanal, and N-heptanal, under conditions favorable to the formation of monoalkyl derivatives, failed to reveal any evidence of partial alkylation.

Moser, U.S. Pat. No. 4,369,142, describes a process for the preparation of N-phosphonomethylglycine in which aminomethylphosphonic acid is reacted in aqueous medium with glyoxal in the presence of sulfur dioxide.

In DE 2,725,669 there is disclosed a process for the preparation of secondary amines under hydrogenation conditions in the presence of a catalyst comprising nickel or cobalt and a quaternary ammonium compound. High yields are reported.

Mono-substituted amino acids, such as glycines and alanines, are prepared by a process disclosed in EPO 0079767 wherein a primary amino group and a ketone are reacted under reductive condensation conditions in the presence of a reductant and a hydrogenation catalyst under conditions of elevated temperature and superatmospheric conditions. Nobel metal catalysts are described and the preferred catalyst is palladium on carbon.

H. Yanagawa et al, "Novel Formation of α-Amino Acids and Their Derivatives from Oxo Acids and Ammonia in an Aqueous Medium", *J. Biochem*, 91, 2087–2090 (1982) discloses the reaction of glyoxylic acid with ammonia, methylamine, and ammonium sulfate to make glycine and/or its derivatives. On page 2088 in Table I, the synthesis of various amino acids is disclosed at pH 4 and pH 8 and at temperatures of 27° C. and 105° C. At the bottom of the left column bridging to the top of the right column on page 2088, it is disclosed that acidic pH and low temperatures were more favorable than alkaline pH and high temperatures for the formation of glycine.

J. Kihlberg, "Synthesis of Strombine. A New Method for Monocarboxymethylation of Primary Amines", *Acta Chemica Scandinavica* B 37, 911–916 (1983) discloses the reaction of two equivalents of glyoxylic acid with primary aliphatic and aromatic amines, which proceeds via the initial formation of an intermediate imine compound. In Table I, appearing on page 914, it is disclosed that various starting amines are reacted with 2 equivalents of glyoxylic acid at temperatures between about 25° C. and 70° C.

Although the teachings of the above references, alone or in combination, can be used to produce satisfactory yields of N-phosphonomethylglycine (glyphosate), each of such teachings suffer from one or more disadvantages. Now, there is provided a straightforward process for the production of glyphosate or its derivatives, without the necessity of isolating intermediate products, in high yields and with high selectivity, (i.e. the ratio of glyphosate produced to the theoretical amount based on the phosphonate starting material).

SUMMARY OF THE INVENTION

These and other advantages are achieved by a process for preparing a secondary amine corresponding to the Formula (I)

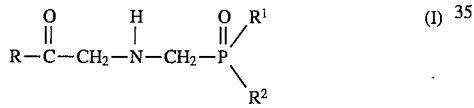

wherein
R, $R^1$, and $R^2$ are independently selected from the group consisting of —OH;
—$OR^3$ wherein $R^3$ is selected from the group consisting of monovalent hydrocarbon groups containing one to about eight carbon atoms;
—$OR^4$ wherein $R^4$ is a herbicidally acceptable salt-forming cation;
the process comprising:
condensing a precursor primary amine corresponding to the formula

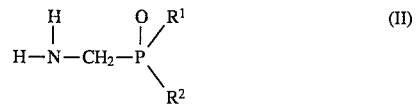

where $R^1$ and $R^2$ are as defined above, in an aqueous reaction medium with an aldehyde hemiacetal, acetal or hydrate thereof, said aldehyde corresponding to the formula

wherein R is as defined above,
reducing without isolation the condensation product to produce the secondary amine of Formula (I),
wherein the condensation and the reduction reactions are carried out at a temperature between about 0° C. and about 120° C.

DETAILED DESCRIPTION OF THE INVENTION

The term monovalent hydrocarbon as used herein includes alkyl, inclusive of both straight and branched chain radicals, such as methyl, ethyl, isopropyl, cyclopropyl, cyclohexyl, tertiary butyl, isobutyl, n-butyl and the various forms of amyl, hexyl, heptyl, octyl, nonyl, decyl, and the like.

Illustrative of herbicidally acceptable salt-forming cations are alkali metals, alkaline earth metals, ammonium, aliphatic ammonium, aliphatic phosphonium, and the like. Most preferred are herbicidally acceptable salt-forming cations which render glyphosate and glyphosate derivatives more readily soluble in water.

In the process, a precursor primary amine corresponding to the Formula (II)

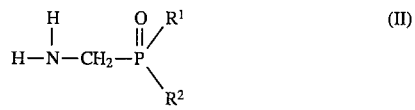

where $R^1$ and $R^2$ are as defined above, is condensed in an aqueous medium with an aldehyde compound or hydrate, hemiacetal or acetal thereof, the aldehyde corresponding to the Formula (III):

where R is as defined above.

In accordance with the present invention, it has been discovered that glyphosate and various glyphosate derivatives can be produced with very high selectivity by the reductive alkylation of aminomethylphosphonic acid, its salts or its esters, in an aqueous medium with a carbonyl compound, such as, for example, glyoxylic acid, a glyoxylate salt, or a related ester thereof. In the process of the invention, contrary to the results reported for the reductive alkylation of glycine with linear aldehydes such as acetaldehyde or butyraldehyde, high conversions of the reactants to the monoalkylated product can be achieved with relatively minimal dialkylation. Thus, not only high selectivity but also good overall yields are obtained. In the aqueous reaction medium, reduction of the intermediate reaction product is carried out either by catalytic hydrogenation, electrochemical reduction or chemical reduction.

Generally, R, $R^1$ and $R^2$ should not include moieties which are reactive with each other to any significant extent under the conditions of the reductive alkylation, nor should these groups include moieties preferentially reactive under such conditions with either the amine or aldehyde of Formula (III) involved in the reductive alkylation.

In accordance with the process of the invention, the amine compound of Formula (II) (such as aminomethylphosphonic acid) and the aldehyde of Formula (III) (such as glyoxylic acid) are dissolved in an aqueous medium and thereafter reacted under reducing conditions either via catalytic hydrogenation or noncatalytic chemical reduction. The reaction proceeds through condensation of amine and aldehyde to form the aldimino intermediate, followed by in situ reduction of the aldimino group to produce the final product.

Figure 1:
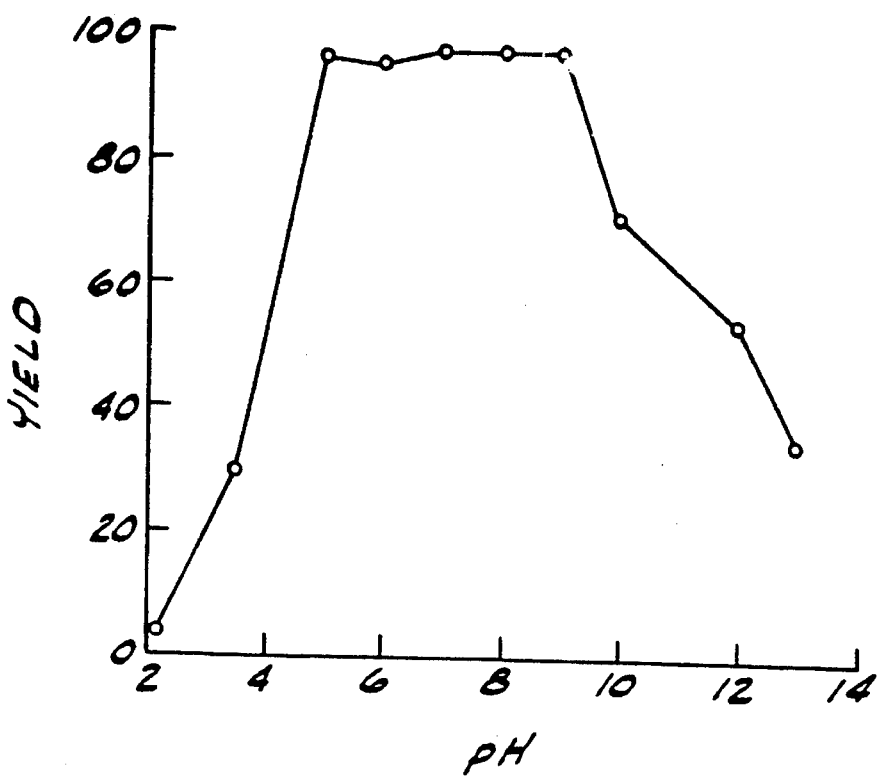
FIG. 1 is a plot of yield of monoalkylated product as a function of the pH of the reaction medium under catalytic hydrogenation conditions.

Prior to carrying out the reductive alkylation by catalytic hydrogenation, preferably the pH of the aqueous solution containing the amine and the aldehyde reactant is adjusted to between 4.0 and about 11.0, preferably 5.0 to 10.0. FIG. 1 illustrates this pH influence on selectivity in the preparation of glyphosate. Adjustment of pH is carried out by addition of a base, typically an alkali metal hydroxide, such as sodium hydroxide or potassium hydroxide. Primary, secondary or tertiary amines, such as tri-ethylamine, can also be used. After adjustment of pH, the aqueous solution is either contacted with hydrogen in the presence of a hydrogenation catalyst or placed in an electrochemical cell where the intermediate formed by the condensation reaction is cathodically reduced.

In the case of catalytic hydrogenation, a wide variety of hydrogenation catalysts may be used, including various transition group metals, such as platinum, palladium, iridium, osmium, rhodium, or ruthenium and various other transition metals such as nickel and cobalt. Other metals, such as copper and zinc, can also be used. Either elemental metals or various compounds of such metals, such as oxides, halides, and organometallics, can be used. Where the catalyst is a solid state material, it can be either supported, such as, for example, platinum on carbon, palladium on alumina, nickel on kieselguhr, etc., or unsupported, for example, Raney nickel or platinum oxide. Various soluble compounds of catalytic metals can also be employed. Palladium on carbon, nickel on kieselguhr, and Raney nickel are particularly effective and convenient catalysts and thus somewhat preferred. But depending on the conditions and nature of the substrate, a number of other catalysts may be equally effective or superior.

The preferred concentration of catalyst also varies widely depending on substrate and conditions. However, the optimum proportion for any particular system can be readily arrived at by routine testing.

Figure 2:
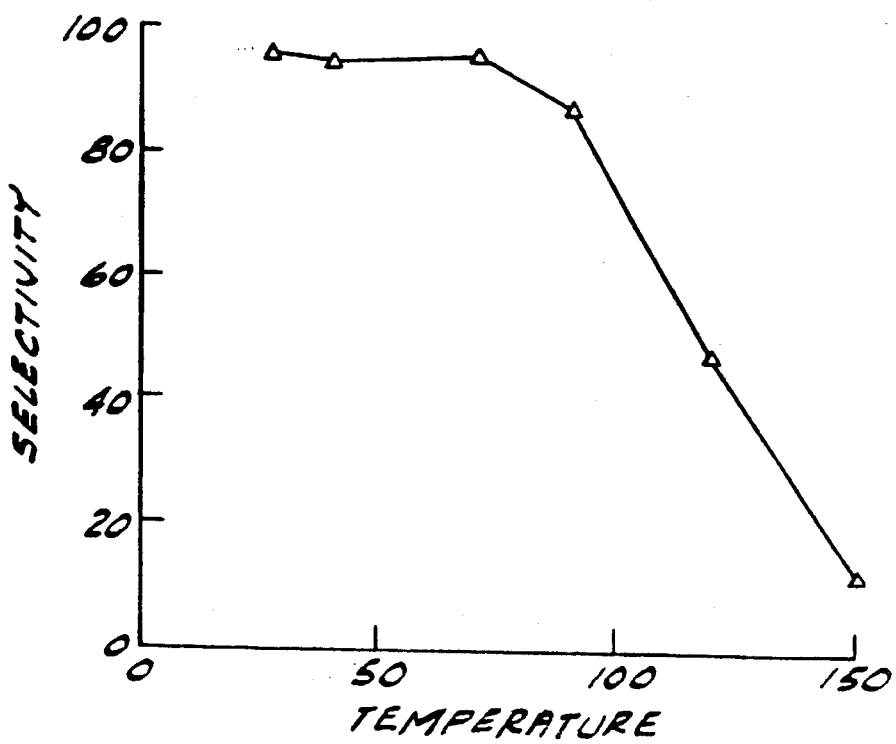
FIG. 2 is a plot of selectivity of monoalkylated product vs. temperature of the reductive alkylation reaction under catalytic hydrogenation conditions.

Broadly, temperatures in the range of 0° C. to 120° C. during the condensation and reduction steps provide good selectivity, although better selectivity is obtained with temperatures in the range of 0° C. to 100° C. It is preferred in the catalytic reduction step to use temperatures between about 20° C. and about 90° C. since selectivity tends to deteriorate at temperatures above about 90° C., as illustrated in FIG. 2. Temperature is less critical where the reductive alkylation of the present invention is carried out by chemical reduction.

Pressure can also be varied widely, with acceptable conversions and selectivity achieved at hydrogen pressures from atmospheric to $6.9 \times 10^6$ Newton/meter$^2$ (N/m$^2$) (1000 psig) or higher.

In order to achieve high selectivity in monoalkylation of primary amines when either catalytic hydrogenation or electrochemical reduction is used, it has not been found necessary to operate with any significant excess of the amine reactant. Substantially equimolar proportions can be used and, in fact, excess of aldehyde compound, for example, an aldehyde to amine ratio of 1.0 to 1.2, or higher is generally preferred. In the chemical reduction step using glyoxylic acid it is preferred to use an amine to aldehyde molar ratio of 1.0 to 2.0, or higher. The concentration of each reactant may vary over a wide range.

In the case of electrochemical reduction, concentrations of reactants, pH, and temperature are governed by essentially the same considerations discussed above. To carry out the electrochemical reductive alkylation, the solution of amine and aldehyde compound is placed in an electrolytic cell, preferably as the catholyte in a cell having a porous barrier between catholyte and anolyte chambers. Such a cell is illustrated, for example, in FIG. 3. This cell includes a container 1 having a porous alumina cup 3 disposed therein. Inside cup 3 is a platinum mesh anode 5. A mercury pool 7, covering the bottom wall 9 of container 1, serves as the cathode. Cup 3 thus divides the cell into anolyte chamber 11 and catholyte chamber 13, respectively. In operating this cell, any convenient electrolyte can be used for the anolyte. Current is applied preferably at a density of approximately 0.001 to 0.5 amps per square centimeter to effect the reduction.

Figure 3:
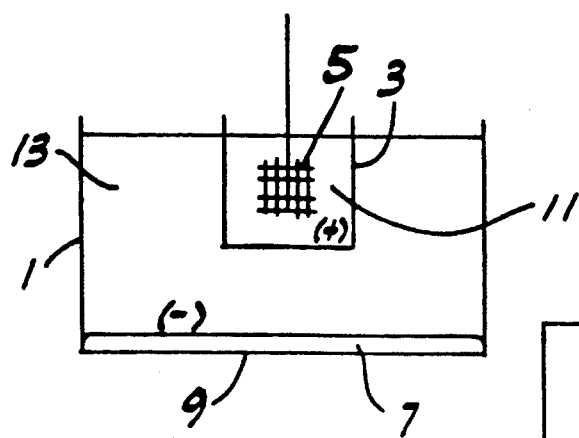
FIG. 3 is a schematic drawing illustrating a cell in which the process of the invention can be carried out via electrochemical reduction.

Electrolytic reduction may also be carried out in an undivided cell whose construction may be essentially identical to that of FIG. 3 except that cup 3 is absent and no separate anolyte liquor is used.

Figure 4:
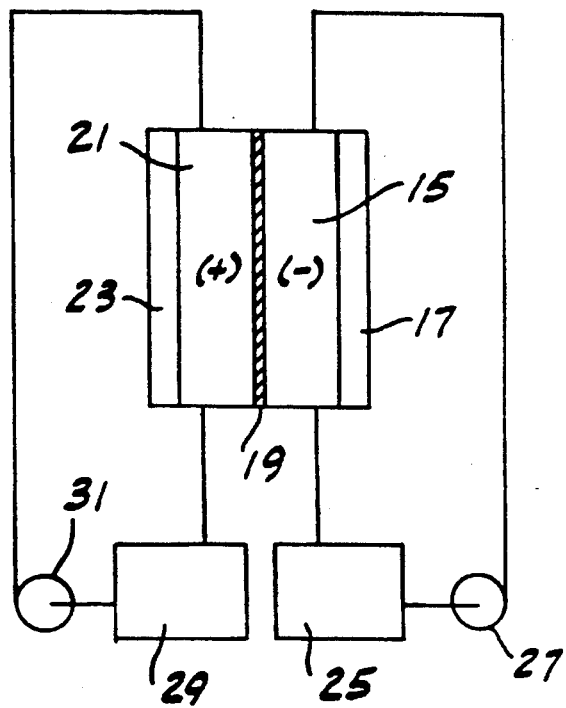
FIG. 4 is a schematic drawing illustrating an alternative cell for carrying out the process of the invention via electrochemical reduction.

Alternatively, electrochemical reduction can take place in a flow cell, such as that illustrated in FIG. 4. In this cell a catholyte flow channel 15 is disposed between a cathode 17 and a semi-permeable membrane 19 which comprises an ion exchange resin. Reaction solution contained in a reservoir 25 is continuously passed through catholyte channel 15 by means of a pump 27. On the opposite side of membrane 19 from channel 15 is an anolyte flow channel 21 and a carbon anode 23. Anolyte solution contained in a reservoir 29 is continuously passed through anolyte channel 21 by means of a pump 31.

The cathode of the electrochemical reduction cell is preferably comprised of a material which exhibits a high hydrogen overpotential in the electrochemical reduction system. Such include, for example, mercury, cadmium, and lead. Other cathode materials, such as palladium, platinum, or graphite may be used. Selection of the anode material is not particularly critical. Thus, for example, the anode may be of platinum, carbon, graphite, platinized titanium, stainless steel, etc.

In a further alternative embodiment of the invention, the reductive alkylation can be carried out utilizing a chemical reducing agent that is effective for reducing the aldimine without the necessity of a catalyst. The preferred chemical reducing agent is the excess aldehyde of formula (III). Reducing agents, such as $SO_2$, that are difficult to separate from the end product should be avoided.

In a preferred embodiment of this invention using a chemical reducing agent, one mole of aminomethylphosphonic acid is contacted with at least two moles of glyoxylic acid or an ester or alkali metal salt thereof. Surprisingly, dialkylation does not occur since half of the glyoxylate is consumed as the reducing agent, and the use of less than two moles of gloxylate for each mole of aminomethylphosphonic acid reduces the yield of desired glyphosate proportionally. The reaction can be run at temperatures up to 120° C., and at low pH in a variety of solvents, such as formic acid, acetic acid, or most preferably water.

Product can be recovered from the reaction solution by various conventional methods. Where the reductive alkylation is conducted by catalytic hydrogenation using a solid state catalyst, the first step in product recovery is removal of the catalyst, as by filtration or centrifugation. The recovered catalyst can in most instances be recycled and reslurried with fresh feed solution containing amine and carbonyl compound reactants. Where the reductive alkylation is carried out with a chemical reducing agent such as glyoxylate, the desired product can be recovered by precipitation or crystallization.

The following examples illustrate the invention.

EXAMPLE 1

Aminomethylphosphonic acid (2.22 g; 0.018 mole) and glyoxylic acid hydrate (1.91 g; 0.02 mole) were dissolved in water (approximately 25 ml). The pH of the resulting solution was adjusted to 6.0 by addition of 2.5N sodium hydroxide, after which the volume of the solution was approximately 75 ml. This mixture was transferred to a 6 oz. Fischer-Porter pressure reaction bottle. A Teflon-covered magnetic stirring bar was placed in the reactor and a 10% palladium on carbon catalyst (100 mg) was mixed with the solution contained in the reactor. Thereafter, the reactor was sealed, evacuated, and purged with nitrogen. This evacuation procedure was repeated and the bottle was then pressurized with hydrogen to $3.34 \times 10^5 N/m^2$ gauge (48 psig). The reaction was allowed to continue overnight, after which the solution was analyzed by nuclear magnetic resonance spectroscopy, and high performance liquid chromatography (HPLC) for N-phosphonomethylglycine (partial sodium salt). The analysis showed that 2.77 g of this product had been produced representing a yield of 91.1% based on aminomethylphosphonic acid. The product was analyzed by proton nmr and had the following characteristics: $^1$H nmr (20% aq. HCl, DSS, 60 MHz) a doublet (2H) centered at $3.54\delta(J_{HCP}=13 Hz)$; a singlet (2H) at $4.12\delta$.

EXAMPLE 2

N-phosphonomethylglycine (glyphosate) was prepared using the apparatus and procedure described in Example 1, except that the initial hydrogen pressure was $6.89\times10^6 N/m^2$ gauge (1000 psig). After 2 hours at room temperature, N-phosphonomethylglycine (sodium salt) was obtained in 90.7% yield based on aminomethylphosphonic acid.

EXAMPLE 3

N-phosphonomethylglycine (glyphosate) was prepared using the apparatus and procedure described in Example 1, except that the catalyst loading was 0.20 g and the reaction was carried out at 50° C. After 5 hours, the conversion of aminomethylphosphonic acid was 74%, and the selectivity of N-phosphonomethylglycine (sodium salt) was 73%.

EXAMPLE 4

Glyphosate was prepared in the manner generally described in Example 2, except that the catalyst employed was 60% to 62% nickel on kieselguhr (0.3 g) obtained from Aldrich Chemical Company. After 4 hours at room temperature, the conversion of aminomethylphosphonic acid was 62.6%, and the selectivity of conversion to the partial sodium salt of glyphosate was 97.6%.

EXAMPLE 5

Glyphosate was prepared in the manner generally described in Example 2, except that the catalyst loading was 0.2 g of 10% palladium on carbon, and the pH was adjusted to 6.0 by dropwise addition of triethylamine rather than sodium hydroxide. After 5 hours of hydrogenation reaction at room temperature, the conversion of aminomethylphosphonic acid to N-phosphonomethylglycine (triethylamine salt) was 100%, and the selectivity of the reaction was 89%.

EXAMPLE 6

Aminomethylphosphonic acid was reductively alkylated by reaction with glyoxylic acid hydrate under catalytic hydrogenation conditions in the manner generally described in Example 2, except that the hydrogenation catalyst was ruthenium metal powder (0.5 g). After 21 hours of reaction at room temperature, the product was analyzed. A 12% conversion of aminomethylphosphonic acid to glyphosate was achieved with a 27.4% selectivity.

EXAMPLE 7

Aminomethylphosphonic acid was reductively alkylated with glyoxylic acid hydrate under catalytic hydrogenation conditions in the manner described in Example 2, except that the catalyst used was palladium metal (0.05 g), and the pH of the initial reaction mixture was 4.5. A 27% conversion of aminomethylphosphonic acid was obtained with a 93.7% selectivity to glyphosate.

EXAMPLE 8

Glyphosate was produced in the manner described in Example 7, except that the initial pH was 6.0. A 30% conversion of aminomethylphosphonic acid and a 100% selectivity to glyphosate salt were observed.

EXAMPLE 9

The reaction of Example 7 was repeated, except that the initial pH was 3.5 and the catalyst was palladium metal (0.5 g). After 38% conversion, a 77% selectivity to glyphosate was observed.

EXAMPLE 10

Glyphosate was produced in the manner described in Example 2, except that one equivalent of methyl glyoxylate (monomeric) was used in place of glyoxylic acid. After 16 hours of reaction, the hydrogen remaining in the reactor was vented and the catalyst removed by filtration. Concentrated hydrochloric acid (approximately 100 ml) was added to the reaction solution which was thereafter refluxed for three hours at atmospheric pressure. Analysis of the reaction solution indicated an 82.1% conversion of aminomethylphosphonic acid and an 84% selectivity to glyphosate.

EXAMPLE 11

The reaction of Example 10 was repeated, except that polymeric methyl glyoxylate was used in place of methyl glyoxylate monomer. Reaction was carried out at 85° C. for 16 hours. The product was hydrolyzed with aqueous HCl. Analysis of the resulting reaction mixture revealed a 71% conversion of aminomethylphosphonic acid with an 80% selectivity to glyphosate.

EXAMPLE 12

Aminomethylphosphonic acid and glyoxylic acid hydrate were reacted under catalytic hydrogenation conditions in the manner described in Example 2, except prior to introduction of hydrogen, the pH was adjusted to 8.0. A 96% yield of glyphosate was obtained.

EXAMPLE 13

Aminomethylphosphonic acid (1.64 g; 0.015 mole) and glyoxylic acid (1.90 g; 0.02 mole) were dissolved in water (30 ml). The pH of the resulting solution was adjusted to 6.0 by addition of dilute aqueous sodium hydroxide. The solution was then transferred to an undivided electrochemical cell equipped with a 7.0 cm$^2$ mercury cathode and a platinum anode. Current was then passed through the cell at 100 milliamperes for a period of 3 hours and 15 minutes. A 35.0% current efficiency was observed in the conversion of starting materials to glyphosate salt.

EXAMPLE 14

Aminomethylphosphonic acid was reductively alkylated with polymeric methyl glyoxylate under catalytic hydrogenation conditions as described in Example 11, except that the reaction was carried out at 70° C., and the pH was initially adjusted to 7.0. After completion of the catalytic hydrogenation step, the product was hydrolyzed by addition of aqueous hydrochloric acid. The resulting reaction mixture was found to contain 2.53 g of glyphosate, reflecting a conversion of aminomethylphosphonic acid of 92.8% and a selectivity to glyphosate of 90.6%.

EXAMPLE 15

Reaction was carried out in the manner described in Example 2, except that the pH was 8.0 and the reaction temperature was 40° C. After 3 hours the reaction was terminated and the reaction product analyzed. A 79.7% conversion of aminomethylphosphonic acid and a 96.6% selectivity to glyphosate salt were observed.

EXAMPLE 16

Reaction was carried out in the manner described in Example 15, except that the aqueous solution of aminomethylphosphonic acid and glyoxylic acid hydrate was heated to 70° C. under an argon atmosphere prior to pressurization with hydrogen, and the reaction was thereafter carried out at 70° C. After 3 hours the reaction was terminated and the reaction product analyzed. A 74.8% conversion of aminomethylphosphonic acid and a 97.1% selectivity to glyphosate salt were observed.

EXAMPLE 17

The reaction was carried out in the manner described in Example 16 except that a reaction temperature of 120° C. was utilized. After 3 hours the reaction was terminated and the reaction product analyzed. A 56.2% conversion of aminomethylphosphonate was obtained with a 49% selectivity to glyphosate.

EXAMPLE 18

Reaction was carried out in the manner described in Example 15, except that the system was preheated to 90° C. and the reaction was carried out at that temperature for 2 hours. An 84.7% conversion and an 88.1% selectivity were found.

EXAMPLE 19

The reaction was carried out in the manner described in Example 16, except that a reaction temperature of 150° C. was maintained. After 3 hours 55.7% of the aminomethylphosphonate starting material had been converted with a 13.8% selectivity to glyphosate.

Set forth in Table I is a summary of data on the effect of temperature on selectivity for reductive alkylation of aminomethylphosphonic acid with methyl glyoxylate, run at a pH of 8.0 and 6.89×10$^6$N/m$^2$ gauge (1000 psig) hydrogen pressure. A plot of this data is set forth in FIG. 2.

TABLE I

| Example No. | Temp. (°C.) | Selectivity (%)* |
| --- | --- | --- |
| 12 | 27 | 96 |
| 15 | 40 | 96.6 |
| 16 | 70 | 97.1 |
| 18 | 90 | 88.1 |
| 17 | 120 | 49 |
| 19 | 150 | 13.8 |

*Selectivity is defined as the ratio of the amount of glyphosate produced to the theoretical amount of glyphosate which could be produced based on the aminomethylphosphonic acid starting material converted.

EXAMPLE 20

Aminomethylphosphonic acid was reductively alkylated with glyoxylic acid under the conditions described in Example 2, except that the catalyst comprised 1% palladium on carbon (0.10 g), and the pH was 8.0. After reaction for 5 hours at room temperature, the hydrogen was vented from the reactor and the reaction solution analyzed. A 40.0% conversion of aminomethlphosphonic acid starting material was observed with a selectivity to glyphosate of 100%.

EXAMPLE 21

The reaction conditions of Example 2 were repeated, except that the catalyst used was 10% palladium on carbon (0.1 g), and the pH was 7.0. After 14 hours of reaction, the reaction product was analyzed. A 97.7% yield of glyphosate was obtained.

Set forth in Table II below is a summary of the effect of pH on yield for reactions run at room temperature and 60.8×10$^5$N/m$^2$ gauge (88 psig) hydrogen pressure. The plot of these data is set forth in FIG. 1.

TABLE II

| pH | Yield (%)* |
| --- | --- |
| 2.2 | 4 |
| 3.5 | 35 |
| 5.0 | 96 |
| 6.0 | 96.7 |
| 7.0 | 97.7 |
| 8.0 | 96 |
| 9.0 | 100 |
| 10.0 | 71 |
| 12.0 | 56 |
| 13.0 | 32 |

*The yield is defined as the ratio of the amount of glyphosate obtained to the theoretical amount of glyphosate obtainable based on the total initial charge of aminomethylphosphonic acid.

EXAMPLE 22

Aminomethylphosphonic acid (3.12 g, 0.028 mol) was dissolved in 30 ml of stirred 98% formic acid maintained at 80° C. with an oil bath. Glyoxylic acid hydrate (5.60 g, 0.061 mol) was added to the solution in several portions, resulting in vigorous gas evolution. After one hour, the reaction flask was removed from the oil bath and the solvent removed on a rotary evaporator to afford crude N-formyl-N-phosphonomethylglycine as a viscous yellow oil.

$^1$H NMR (D$_2$O): δ 8.3(s), 8.15(s), 4.4(s), 4.3(s), 3.79 (d, J=12 Hz), 3.75 (d, J=10 Hz).

$^{31}$P NMR (D$_2$O): δ 17.0 (t, J=12 Hz), 16.1 (t, J=10 Hz)

The crude oil was dissolved in 30 ml of 12% HCl and heated at reflux for four hours. The reaction was allowed to cool to room temperature, during which time a white solid precipitated from solution. This solid (2.54 g) was collected by filtration and identified by $^1$H NMR as glyphosate. Medium pressure liquid chromatography of the mother liquor on a Dowex 50×8–400 ion exchange column afforded an additional 1.88 g of glyphosate. The combined glyphosate fractions weighed 4.42 g and were determined by HPLC assay to contain 98.75 wt % glyphosate. The actual isolated yield of glyphosate was therefore 92.2%

EXAMPLE 23

The reaction of aminomethylphosphonic acid and glyoxylic acid was carried out as described in Example 22 except that 90% formic acid was used as the solvent. After hydrolysis, 4.45 g of crude product was isolated as an offwhite solid by crystallization and subsequent chromatography of the mother liquor. This solid was 96.19 wt % glyphosate as determined by HPLC assay. The actual yield of glyphosate was therefore 90.5%.

EXAMPLE 24

The reaction of aminomethylphosphonic acid and glyoxylic acid was carried out as described in Example 22 except that glacial acetic acid was used as the solvent. After hydrolysis of the intermediate N-formyl-N-phosphonomethylglycine, 4.62 g of crude product was isolated by crystallization and subsequent chromatography of the mother liquor as an offwhite solid. HPLC assay showed the solid to contain 98.16 wt % glyphosate. The actual yield of glyphosate was therefore 95.8%

EXAMPLE 25

Aminomethylphosphonic acid (5.50 g, 0.05 mol) was dissolved in 50 ml of water maintained at 95°–100° C. Glyoxylic acid hydrate (9.70 g, 0.105 mol) was added in one portion. After 8 hours of reaction time, the water was removed on a rotary evaporator to afford a brown semisolid. Trituration of this semisolid with a small amount of water followed by filtration afforded 6.43 grams of glyphosate as a crude white solid. An additional 1.60 grams of glyphosate was recovered by chromatography of the mother liquor as described in Example 22. The total yield of crude product, which was shown by HPLC to contain 98.87 wt % glyphosate, was 8.03 grams. The actual yield of glyphosate was therefore 94.0%.

EXAMPLE 26

Aminomethylphosphonic acid (1.9 g, 0.017 mol) and glyoxylic acid methyl ester methyl hemiacetal (4.5 g, 0.038 mol) were heated at reflux in 25 ml of 37% HCl for 20 hours. The solvent was removed on a rotary evaporator to give crude glyphosate as an oily solid. The crude glyphosate was purified by ion exchange chromatography (Dowex 50×8–400) using water as the eluent to yield 2.6 g (89.6%) of glyphosate.

As various changes could be made in the above methods and products without departing from the scope of the invention, it is intended that all matter contained in the above description or shown in the accompanying drawings shall be interpreted as illustrative and not in a limiting sense.

What is claimed is:

1. A process for preparing N-phosphonomethylglycine or an agronomically acceptable salt thereof comprising the steps of:

condensing aminomethylphosphonic acid in an aqueous reaction medium with a pH between 5 and 11 with glyoxylic acid or a hemiacetal, acetal or hydrate thereof, and reducing without isolation the condensation product to produce N-phosphonomethylglycine, wherein said reduction is carried out electrochemically at a temperature between 0° C. and 100° C.

2. The process of claim 1 wherein the electrochemical reduction is carried out at a temperature between about 20° C. and about 90° C.

3. The process of claim 2 wherein the pH is between 5 and 10.

4. The process of claim 1 wherein the molar ratio of glyoxylic acid or a hemiacetal, acetal or hydrate thereof to aminomethylphosphonic acid is equal to or greater than 1.0.

5. The process of claim 4 wherein the molar ratio of glyoxylic acid or a hemiacetal, acetal or hydrate thereof to aminomethylphosphonic acid is between 1.0 and 2.0.

6. The process of claim 5 wherein glyoxylic acid is reacted with aminomethylphosphonic acid.

7. A process for preparing N-phosphonomethylglycine or an agronomically acceptable salt thereof comprising the steps of:

condensing aminomethylphosphonic acid in an aqueous reaction medium with a pH≧5 with glyoxylic acid or a hemiacetal, acetal or hydrate thereof, and reducing without isolation the condensation product to produce N-phosphonomethylglycine, wherein said reduction reaction is carried out by catalytic hydrogenation at a temperature≦100° C.

8. The process of claim 7 wherein the hydrogenation catalyst is selected from the group consisting of platinum, palladium, osmium, iridium, rhodium, nickel, cobalt, and combinations of these metals, and their salts or oxides.

9. The process of claim 7 wherein the catalytic hydrogenation is carried out at temperature between about 20° C. and about 90° C.

10. The process of claim 9 wherein the pH is between 5 and 10 and said hydrogenation catalyst is platinum or palladium.

11. The process of claim 7 wherein the molar ratio of glyoxylic acid or a hemiacetal, acetal or hydrate thereof to aminomethylphosphonic acid is equal to or greater than 1.0.

12. The process of claim 11 wherein the molar ratio of glyoxylic acid or a hemiacetal, acetal or hydrate thereof to aminomethylphosphonic acid is between 1.0 and 2.0.

13. The process of claim 12 wherein glyoxylic acid is reacted with aminomethylphosphonic acid.

\* \* \* \* \*

UNITED STATES PATENT AND TRADEMARK OFFICE
CERTIFICATE OF CORRECTION

PATENT NO.     :     5,578,190

DATED           :     November 26, 1996

INVENTOR(S)  :     Thomas E. Rogers and Lowell R. Smith

It is certified that error appears in the above-identified patent and that said Letters Patent is hereby corrected as shown below:

In claim 7, column 12, line 39 of the patent, before the second occurrence of "with" and following "pH", please delete "$\geq 5$" and insert therefor --between 5 and 11--.

In claim 7, column 12, line 44 of the patent, before "100" and following "temperature", please delete "$\leq$" and insert therefor --between 0°C and--.

Signed and Sealed this

First Day of July, 1997

*Attest:*

BRUCE LEHMAN

*Attesting Officer*     *Commissioner of Patents and Trademarks*